US006465216B2

(12) United States Patent
Laible et al.

(10) Patent No.: US 6,465,216 B2
(45) Date of Patent: Oct. 15, 2002

(54) METHODS AND CONSTRUCTS FOR EXPRESSION OF FOREIGN PROTEINS IN PHOTOSYNTHETIC ORGANISMS

(75) Inventors: Philip D. Laible, Villa Park; Deborah K. Hanson, Downers Grove, both of IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/775,345

(22) Filed: Feb. 1, 2001

(65) Prior Publication Data

US 2002/0102655 A1 Aug. 1, 2002

(51) Int. Cl.[7] ................ C07H 21/04; C12P 21/00; C12N 1/21; C12N 15/74
(52) U.S. Cl. ........... 435/69.1; 435/69.7; 435/252.1; 435/252.3; 435/471; 435/476; 435/4; 435/6; 435/7.1; 435/7.2; 536/23.1; 536/23.2; 536/23.4; 536/23.7; 536/24.1
(58) Field of Search ............... 435/69.1, 69.7, 435/4, 5, 6, 7.1, 7.4, 455, 471, 252.1, 252.3, 476; 536/23.1, 23.2, 23.4, 23.7, 24.1

(56) References Cited

U.S. PATENT DOCUMENTS 6,017,754 A * 1/2000 Chesnut et al. .......... 435/320.1

OTHER PUBLICATIONS

Ralf van Dijk et al, The methylotrophic yeast Hansenula polymorpha: a versatile cell factory, Enzyne and Microbial Technology 26 (2000) 793–800.*

* cited by examiner

Primary Examiner—David Guzo
(74) Attorney, Agent, or Firm—Cherskov & Flaynik

(57) ABSTRACT

A method for expressing and purifying foreign proteins in photosynthetic organisms comprising the simultaneous expression of both the heterologous protein and a means for compartmentalizing or sequestering of the protein.

27 Claims, 12 Drawing Sheets

METHODS AND CONSTRUCTS FOR EXPRESSION OF FOREIGN PROTEINS IN PHOTOSYNTHETIC ORGANISMS

CONTRACTUAL ORIGIN OF THE INVENTION

The United States Government has rights in this invention under Contract No. W-31-109-ENG-38 between the U.S. Department of Energy and the University of Chicago representing Argonne National Laboratory.

BACKGROUND OF THE INVENTION

1. Field of the Invention

This invention relates to a method for producing protein, and more specifically this invention relates to a method for expressing and isolating heterologous proteins using photosynthetic organisms.

2. Background of the Invention

Proteins are routinely divided into soluble proteins and membrane proteins. Membrane proteins are extremely important for normal cell function. They provide the means by which cells communicate, transduce signals and transport metabolites between internal compartments, and build gradients of ions which are used to fuel all ingrained activities. Membrane proteins are one of the early defenses against invading foreign organisms.

Although roughly 35% of the proteins known or expected to be found in most organisms are membrane-associated, little structural or functional information exists on these proteins relative to their soluble peers. Any new information on membrane protein structures would aid biologists, physicists and chemists in their understanding of important structural relationships necessary for essential protein functions in lipid bilayer environments. Using traditional methodology, it has been difficult to purify quantities of native membrane-associated proteins that are sufficient for experiments. Inasmuch as the functional properties and stability of membrane proteins are dependent upon the lipid micelle surrounding them, these proteins often denature or otherwise deviate from their native states when removed from their natural environs. Additionally, most membrane proteins are most commonly expressed at very low levels, in amounts insufficient for purification and crystallization. To date, the three dimensional structures of only a dozen unique membrane proteins are known, in comparison to the structures of approximately 1500 soluble proteins.

Knowledge of the structures and a determination of the function of membrane proteins would contribute greatly to our understanding of biological processes. For example, in recent years, structure-based rational drug design has produced powerful competitive inhibitors of cofactor binding in enzyme catalysis. Because of their importance in cellular functions that can contribute to various disease states, membrane proteins are targets for drug discovery that impacts disease control and prevention.

Purification of membrane proteins from their native host cells has been attempted by removing the protein from its native (hydrophobic) surroundings and placing same in small detergent micelles which attempt to mimic the lipid environment. Following this solubilization process, routine chromatography or precipitation techniques (which have been perfected for soluble proteins) are utilized to purify and crystallize the solubilized membrane proteins. Such adaptations rarely yield large amounts of the membrane protein in functional form.

Efforts have been made to create a process whereby membrane-associated proteins are over-expressed and subsequently purified from native hosts or host cells of another organism (i.e., heterologous expression). To some degree, these efforts have all utilized a combination of a desired coding sequence with a foreign promoter known to induce high levels of protein synthesis. For example, U.S. Pat. No. 5,310,663 (Dobeli et al.) describes fusion proteins, comprising a coding sequence of a desired protein and the coding gene sequence of an affinity peptide, wherein the affinity peptide is attached and used to purify the desired protein product. Purification is accomplished using metal chelate affinity chromatography in nitrilotriacetic acid resins. However, no provision exists for circumventing the unique and inherent difficulties associated with purifying intact hydrophobic proteins.

U.S. Pat. No. 5,750,374 (Dobeli et al.) provides a process for producing hydrophobic polypeptides and proteins by using the fusion protein technology of the prior '663 patent. Like the '663 patent, this process links a coding gene sequence of a desired protein with the coding sequence of an affinity peptide to create a fusion protein. This process provides an additional means of purifying the desired protein through chemical or enzymatic cleavage at a strategic cleavage site. However, the '374 patent has no provision for maintaining the intact, tertiary and quaternary structure of the desired hydrophobic protein.

A method for the heterologous overexpression of hydrophobic proteins has been disclosed by Turner et al. *Protein Expression and Purification,* 17, pp. 312–323 (1999). Coding regions of desired membrane proteins are juxtaposed with the bacterio-opsin (bop) regulatory sequences in the cell membrane of *Halobacterium salinarum.* While attempts at overexpression have been successful, this process does not provide for simultaneous production and sequestration or compartmentalization of the desired protein.

R. van Dijk et al. *Enzyme and Microbial Technology* 26 9–10, pp 793–800 describe a heterologous overexpression system based on *Hansenula polymorpha.* This method suggests the utilization of peroxisomes in which produced proteins may accumulate. However, as with the *H. salinarum* system discussed supra, no provision exists for the simultaneous production and compartmentalization of the targeted components, inasmuch as the promoters utilized there in are for the most part constitutive.

A need exists in the art for a generalized system for the heterologous expression and recovery of functional membrane proteins. Ideally, the system should incorporate a means to control inducement of expression of the proteins which is simultaneous with the sequestration and therefore isolation of the protein. The system also should utilize simple purification protocols.

SUMMARY OF THE INVENTION

It is an object of the present invention to provide a method for heterologous expression of membrane proteins that overcomes many of the disadvantages of the prior art.

It is another object of the present invention to provide a method for purifying proteins. A feature of this method is that synthesis of the protein occurs at the same time a membrane to encapsulate that protein is generated. An advantage of this method is that the generated protein is sequestered in a compartment in its native state while it is produced.

Still another object of the present invention is to utilize a photosynthetic system to produce transmembrane proteins. A feature of this invented method is the utilization of a promoter, which responds to the same environmental cues as do promoters for membrane synthesis, to produce the transmembrane proteins. For example, the invented process utilizes a promoter for proteins of the photosynthetic membrane of Rhodobacter to also facilitate production of the transmembrane protein. An advantage of this method is that well-known "indicators" such as color changes in the Rhodobacter system can be used as a monitor of culture conditions that favor the synthesis of heterologous proteins from the inducible promoter.

Yet another object of the present invention is to provide a method for purifying transmembrane proteins. A feature of this invented method is to append an affinity tag to the protein. An advantage of the invented method is that the tag facilitates simple, rapid, and less disruptive extraction of the formed protein from its native membrane environment so that the protein retains its structural and functional integrity for further study.

A further object of the present invention is to provide a method to facilitate the controlled over-expression of heterologous membrane proteins. A feature of the method is that intracytoplasmic membrane (ICM) used to harbor the expressed foreign membrane proteins is both inducible and readily isolated. The extent of induction, and thus the amount of foreign protein that is synthesized, can be adjusted continuously. An advantage of the method is that this parallel induction of both the foreign membrane protein and its preferred environment will favor insertion of the expressed membrane protein into newly developing ICM, thereby decreasing the chances of inclusion body formation. Another advantage is that the same culture manipulations can be used at the same time to introduce heavy metal, scattering moieties into the gene products to facilitate subsequent structure determination with multiple-wavelength anomalous dispersion (MAD) techniques.

Briefly, the invention provides a method for production of heterologous proteins comprising simultaneous expression of both the protein and a hospitable environment which facilitates in situ sequestration and therefore rudimentary in vivo purification of the protein.

The invention also provides a method for simultaneously producing and sequestering proteins, including functional membrane proteins.

The invention further provides a method for simultaneously producing and compartmentalizing a fusion protein, the method comprising selecting a photosynthetic organism having promoters for producing a membrane compartment; placing expression of the fusion protein under the control of one of these promoters; and activating that promoter.

Also provided is a DNA sequence that will transcribe as mRNA, the sequence comprising a puf-promoted or a puc-promoted gene that will result in a stable transcript and the translation of biologically active polypeptides linked to an affinity peptide, and that will also result in the simultaneous isolation/purification of the polypeptides in their native state.

Further provided are DNA sequences that will transcribe as mRNA comprising an RNA stem-loop stabilizing region; and a transcript attached to said region that will result in the translation of biologically active polypeptide linked to an affinity peptide, and that will result in the simultaneous compartmentalization of the polypeptide in its native state.

Also provided is a method to identify products of genes which interact to form stable, multi-subunit membrane-associated protein complexes.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
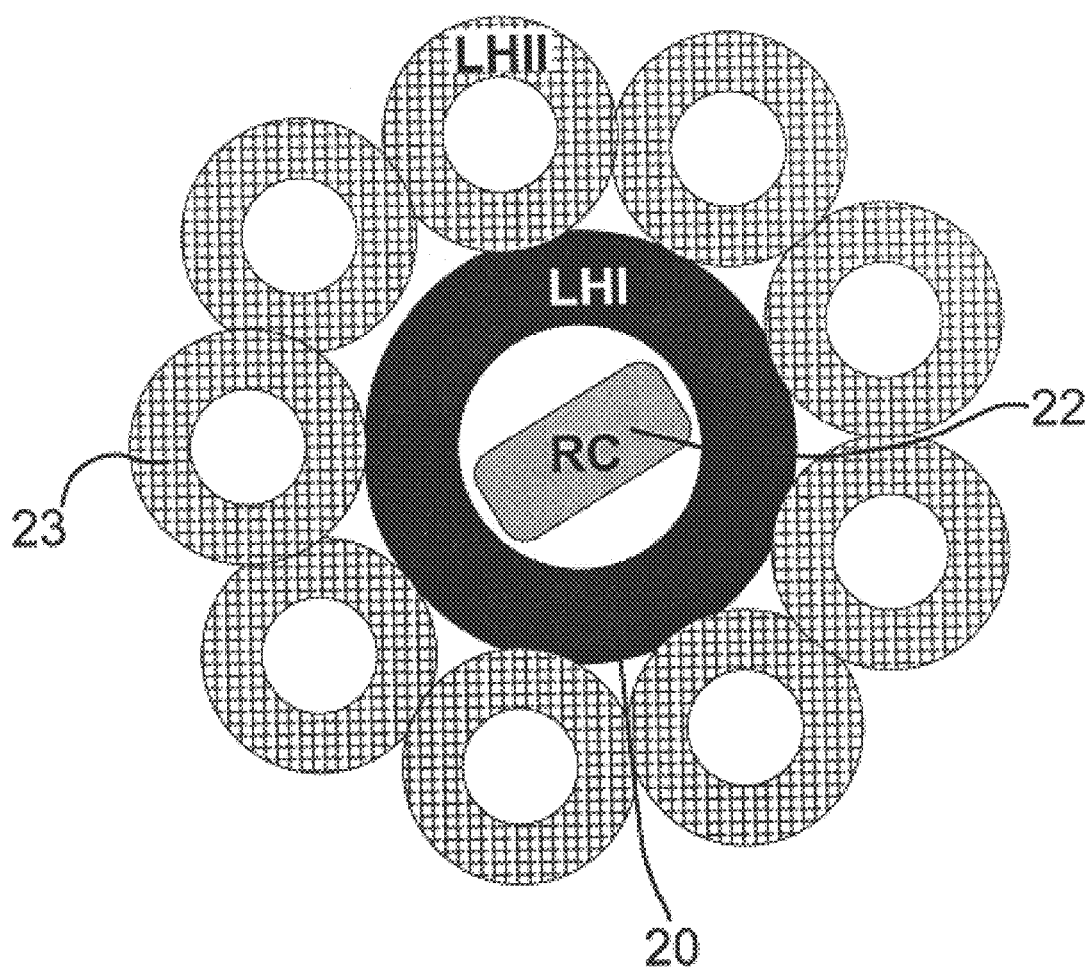
FIG. 1 is a structural model for the arrangement of light-harvesting antennae around reaction centers in photosynthetic bacterial membranes.

A protocol has been developed to facilitate the parallel induction of foreign membrane protein and host membrane. The invented method simultaneously creates a heterologous protein and encapsulates that protein in its native state. The protein can be one protein, separate proteins, or a complex of mutually co-dependent proteins, such as a multi-subunit membrane-associated protein complex.

The invented protocol allows for the use of different promoters, which respond to the same environmental stimuli, (by actuating target promoters) to simultaneously induce foreign protein formation and sequestration. The co-expressed intracytoplasmic membrane (ICM) serves as a means to simultaneously compartmentalize, and therefore segregate, the developing heterologous membrane-bound proteins from the majority of other cellular components. The system has also produced functional, soluble proteins from genes derived from an unrelated organism.

In addition, the photosynthetic cells used in this protocol can be induced to incorporate scattering moieties incorporating heavy metals, such as seleno-methionine, so as to facilitate structure determination in anomalous diffraction experiments. And the method can be used to provide moieties to aid in isolation and purification of the induced proteins.

Broad-host-range plasmids have been engineered to facilitate the cloning, expression and purification process. The purification of soluble proteins tethered to proteins of the developing intracytoplasmic membrane proteins also is facilitated.

A myriad of photosynthetic hosts is suitable for use in the invented method. Photo-synthetic bacteria, photosynthetic algae, and unicellular photosynthetic organisms are appropriate. Specifically, bacteria which produce large amounts of internal membranes are suitable host organisms.

Any organism (such as Rhodobacter) which produces dynamic membranes is particularly suitable, inasmuch as these membranes allow the organism to respond to the environment surrounding it. Strains to be used as expression hosts are selected or engineered to contain a partial to full complement of proteins native to their respective ICM in order to optimize yield of the foreign proteins. The following species are suitable candidates:

Green Sulfur Bacteria
*Chlorobium limicola*
*Chlorobium vibrioforme*
*Chlorobium phaeobacteriodes*
*Chlorobium phaeovibrioides*
*Chlorobium chlorovibrioides*
*Chlorobium tepidum*
*Prosthecochloris aestuarii*
*Prosthecochloris phaeoasteriodes*
*Ancalochloris perfilievii*
*Pelodictyon luteolum*
*Pelodictyon clathratiforme*
*Pelodictyon phaeum*
*Pelodictyon phaeoclathratiforme*
*Chloroherpeton thalassium*
Purple and Green Bacteria
*Thiospirillum jenense*
*Thiorhodovibrio winogradskyi*
*Chromatium okenii*
*Chromatium weissei*
*Chromatium warmingii*
*Chromatium buderi*
*Chromatium tepidum*
*Chromatium minus*
*Chromatium salexigens*
*Chromatium vinosum*
*Chromatium violascens*
*Chromatium gracile*
*Chromatium minutissimum*
*Chromatium purpuratum*
*Thiocystis violacea*
*Thiocystis gelatinosa*
*Lamprocystis roseopersicina*
*Lamprobacter modestohalophilus*
*Thiodictyon elegans*
*Thiodictyon bacillosum*
*Amoebobacter roseus*
*Amoebobacter pendens*
*Amoebobacter pedioformis*
*Amoebobacter purpureus*
*Thiopedia rosea*
*Thiocapsa roseopersicina*
*Thiocapsa pfennigii*
*Thiocapsa halophila*
*Ectothiorhodospira mobilis*
*Ectothiorhodospira shaposhnikovii*
*Ectothiorhodospira vacuolata*
*Ectothiorhodospira halophila*
*Ectothiorhodospira halochloris*
*Ectothiorhodospira abdelmalekii*
*Ectothiorhodospira marismortui*
*Rhodosprillum rubrum*
*Rhodosprillum photometricum*
*Rhodosprillum molischianum*
*Rhodosprillum fulvum*
*Rhodosprillum salexigens*
*Rhodosprillum salinarum*
*Rhodosprillum mediosalinum*
*Rhodosprillum centenum*
*Rhodosprillum sodomense*
*Rhodopila globiformis*
*Rhodomicrobium vannielii*
*Rhodobacter capsulatus*
*Rhodobacter veldkampii*
*Rhodobacter sphaeroides*
*Rhodobacter sulfidophilus*
*Rhodobacter euryhalinus*
*Rhodobacter adriaticus*
*Rhodopseudomonas palustris*
*Rhodopseudomonas viridis*
*Rhodopseudomonas sulfoviridis*
*Rhodopseudomonas blastica*
*Rhodopseudomonas acidophila*
*Rhodopseudomonas marina*
*Rhodopseudomonas julia*
*Rhodopseudomonas cryptolactis*
*Rhodopseudomonas rosea*
*Rhodocyclus purpureus*
*Rhodocyclus tenuis*
*Rhodoferax fermentans*
*Rubrivivax gelatinosus*
Heliobacter
*Heliobacter chlorum*
*Heliobacter gestii*
*Heliobacter modesticaldum*
*Heliobacter fasciatum*
*Heliobacter mobilis*
Filamentous Anoxygenic Phototrophs
*Chloroflexus aurantiacus*
Marine Chloroflexus-like organisms
*Heliothrix oregonensis*
Chloronema
Oscillochloris
Aerobic Anoxygenic Phototrophs
*Eythrobacter longus*
Eythrobacter sp. OCh 175
*Roseobacter litoralis*
*Roseobacter denitrificans*
*Methylobacterium rhodesianum*
*Methylobacterium radiotolerans*
*Methylobacterium extorquens*

*Methylobacterium zatmanii*
*Methylobacterium fujisawaense*
*Methylobacterium rhodinum*
*Porphyrobacter neustonensis*
*Porphyrobacter tepidarius*
Rhizobium BTAil
*Acidiphilium rubrum*
*Acidiphilium angustum*
*Acidiphilium cryptum*
*Acidiphilium multivorum*
*Acidiphilium organovorum*
*Erythromicrobium sibiricum*
*Erythromicrobium ezovicum*
*Erythromicrobium hydrolyticum*
*Erythromicrobium ursincola*
*Erythromicrobium ramosum*
*Roseococcus thiosulfatophilum*

Exemplary photosynthetic bacterial systems include Rhodobacter, Rhodopseudomonas, and Rhodospirillum. Various strains which contain a partial to full complement of ICM proteins can be used as expression hosts to optimize yield of the foreign protein.

A preferred system has all of the characteristics of Rhodobacter. Members of the Rhodobacter genus are extremely robust and among the most versatile organisms known to biology. These bacteria are characterized by a metabolic diversity that allows them to adapt readily to a wide variety of environmental conditions. They thrive in dark or well-lit environments, in the presence or absence of oxygen. They can biochemically exploit an assortment of substrates for cell growth and division, or can harvest energy from the sun for that same purpose. As an example, single members of the genus Rhodobacter are known to reduce nitrogen compounds, fix carbon dioxide, utilize carbon sources in an aerobic environment, or grow photosynthetically under anaerobic conditions—depending on resources available in their immediate vicinity. The mechanisms by which environmental cues are sensed and are used to turn on or off the biochemical machinery necessary to survive in a particular setting are complex, as is the composition of the membranes in this organism.

Proteins associated with the inner membranes of Rhodobacter cells (those proteins that adhere to, span, or are tethered to the membrane) are quite dynamic and are a key feature of the multifaceted nature of the organism. This application takes advantage of the robust nature of organisms such as Rhodobacter and their complex and dynamic membrane systems to engineer them to become cellular factories for the production of foreign proteins.

Generally, light induced growth is facilitated in photosynthetic bacteria through the absorption of photons by specialized light-harvesting (LH) complexes, known as antennae.

These antennae transfer excited states to reaction centers (RC) (element 22) where primary charge separation occurs.

FIG. 1 depicts the structural model for the arrangement of light-harvesting antennae around reaction centers contained in photosynthetic bacterial membranes. The model is disclosed in S. Karrasch et al, *EMBO Journal* 14 631, and M. Z. Papiz et al *Trends in Plant Sci.* 1 198. As can be noted in FIG. 1, the RC is situated inside a ring of a single LH1 complex (element 20). The periphery of the LH1 complex is surrounded by antennae of another light harvesting complex (LH2) (element 23). In this arrangement, electronic excited states flow energetically downhill from the outer LH2, 23 to the inner LH1 20 to be photoconverted by the central RC .

Generally, the fragment of host-chromosomal DNA containing the operon for producing the LH/RC machinery is transferred to a vector. The gene for the desired protein is then inserted to replace one or more genes of the operon. When this expression plasmid is transferred back to the photosynthetic host organism, the target protein is generated.

The inventors have found that heterologous protein expression is enhanced when functional native ICM proteins are also present. A sequence encoding a fragment of a native ICM protein may be fused to the end(s) of the foreign protein sequence to enhance targeting and incorporation of the foreign protein to the ICM.

Photosynthetic
Bacteria Detail

For the sake of illustration only, Rhodobacter genus is discussed, infra. Rhodobacter produces large quantities of membrane that is filled with proteins of the photosynthetic apparatus. The inventors have replaced the photosynthetic proteins with foreign membrane proteins. Specifically, the inventors have found that inasmuch as the Rhodobacter genus of photosynthetic bacteria can produce large quantities of intracellular membrane, placing the expression of heterologous proteins under control of a promoter that controls synthesis of intracellular membrane components induces expression of the heterologous protein as well. Among the bacteria in the Rhodobacter genus, *R. sphaeroides*, and *R. capsulatus* are particularly suitable for use in the invented protein production and isolation method.

As noted supra, the Rhodobacter genus of photosynthetic bacteria can be grown in a variety of conditions, such as anaerobic, semi-aerobic, aerobic, light or dark. This is because the cytoplasmic membrane in Rhodobacter contains components of the respiratory chain, transport systems, and other energy-transducing complexes. The physiology of this genus under each of these conditions is different.

Figure 2:
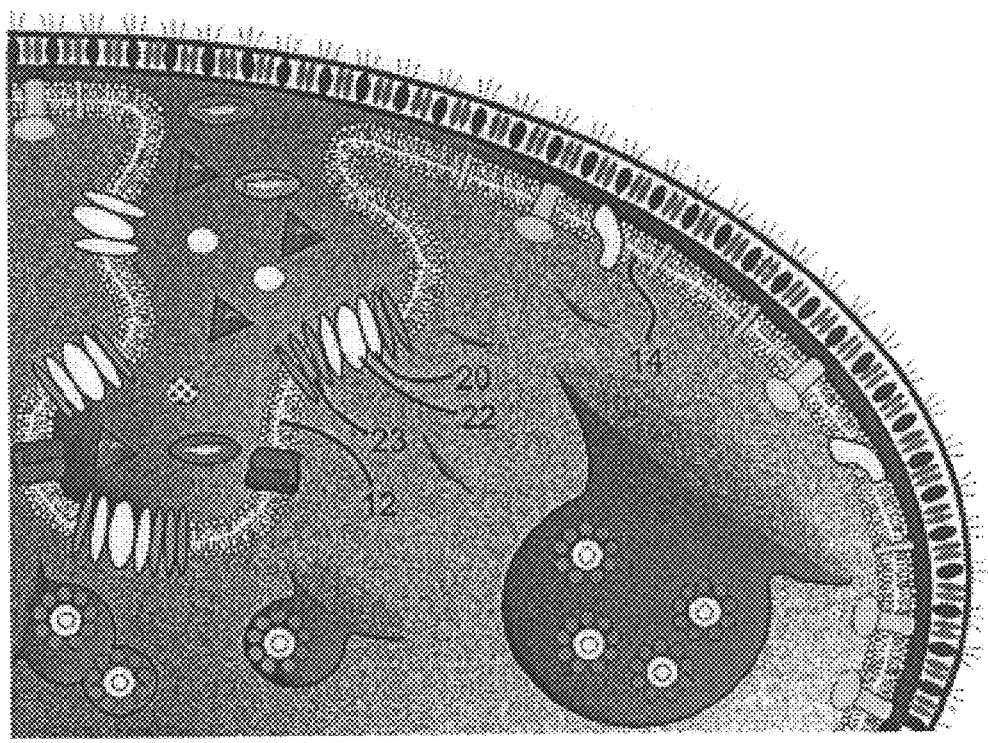
FIG. 2 is a schematic diagram of inducible invaginations of a Rhodobacter cell membrane.

For example, when Rhodobacter cultures are switched from aerobic chemotrophic conditions to phototrophic growth conditions, large quantities of a new intracytoplasmic membrane (ICM) that houses the newly synthesized photosynthetic machinery are induced. The physiological features of the ICM membrane machinery are illustrated in FIG. 2. This ICM is formed as invaginations of the cytoplasmic membrane and in its nascency, is contiguous with the cytoplasmic membrane. Since it houses the newly synthesized photosynthetic machinery of the cell, the lipid, chemical, and protein composition, and its kinetics of biogenesis differ from the cytoplasmic membrane. Rhodobacter can also be induced to synthesize ICM in dark-grown cultures which are limited for oxygen, since this stimulus also directs the organism to prepare for a switch from oxidative phosphorylation to anaerobic phototrophic growth.

The inventors have induced Rhodobacter to synthesize ICM and ICM-protein, either native or foreign. During cell disruption, the ICMs break away from the cytoplasmic membrane to become discrete entities with physical properties that are different from other cellular components. Inasmuch as the cells become pigmented as these ICMs form, the inventors exploited this phenomenon to indicate the presence of heterologous protein formed concomitantly with the ICMs. Therefore, the heterologous proteins residing in the ICMs are easily isolated from other protein-containing cellular fractions. As discussed infra, the inventors have utilized the invented system to express and incorporate human membrane proteins into induced membranes of Rhodobacter.

To facilitate heterologous membrane protein purification (through isolation of the heterologous membrane protein from other ICM components), an affinity tag is engineered into the protein-coding sequence. The affinity tag is used to readily sequester the heterologous membrane proteins in native form by chromatography with the correspondingly compatible resin. This results in a 4–5 hour purification protocol, detailed infra, versus the more than three day isolation procedure provided by the state-of-the-art for the purification of unengineered membrane proteins from native hosts.

In Rhodobacter species, cells become pigmented as the ICM develops. This new membrane takes the form of vesicles. As depicted in FIG. 2, an ICM 12 is contiguous with a cell membrane 14. The interior of these vesicles contains periplasmic components. For example, the white region of the ICM houses the reaction center (RC) 22, which in photosynthetic organisms comprises a central complex of pigments and proteins. The RC is comprised of three separate components, or subunits, called H (heavy), M (medium) and L (light) based on the way these units migrate in an electric field. FIG. 3 depicts genes for subunits L and M. The gray region in FIG. 1 represents the RC complex 22. These RC complexes house the cofactors of the photosynthesis complex, which include bacteriochlorophylls, bacteriopheophytins, quinones and a non-heme iron.

As noted supra, upon cell disruption, the vesicles depicted in FIG. 2 break apart from the cell membrane, thus becoming sealed "inside-out" particles, termed chromatophores. These vesicles (basically ICM) are easily isolated by virtue of their size. Chromatophores are much smaller than cellular debris and thus remain soluble during low-speed centrifugation. Then, during brief ultracentrifugation, they are readily separable from cellular components in forming a pellet. This pellet is rich in ICM. Therefore, proteins residing in the ICM are already significantly purified following these two simple fractionation steps with a total duration of typically less than two hours, and often less than one hour.

Intracytoplasmic Membrane and puf Operon Detail

The intracytoplasmic membrane (ICM) is formed when photosynthetic bacteria are switched from chemotrophic conditions to phototrophic growth conditions or when grown in the absence of light and limited oxygen.

As noted above, the ICM forms from invaginations of the cell membrane and is thus contiguous with the cell membrane, while also having different characteristics vis-a-vis the cell membrane. Most importantly, the ICM differs from the cell membrane in its kinetics of biogenesis. Specifically, the ICM forms when ICM-protein is being actively expressed and folded, an event which occurs separate from the formation of the cell membrane.

The majority of native ICM protein belongs to three transmembrane protein complexes of the photosynthetic apparatus: the reaction center (RC) and the two different light harvesting complexes (LH1 and LH2). The puf operon, designated as element 19 in FIG. 3A, and specifically the puf promoter 21, coordinates expression of Light Harvesting Complex 1 (LH1) and RC complexes. The puc operon, designated in FIG. 3B as numeral 17, coordinates expression of the Light Harvesting Complex 2 (LH2), 23, via its puc promoter 25. The LH1 will be discussed first.

Figure 3A:
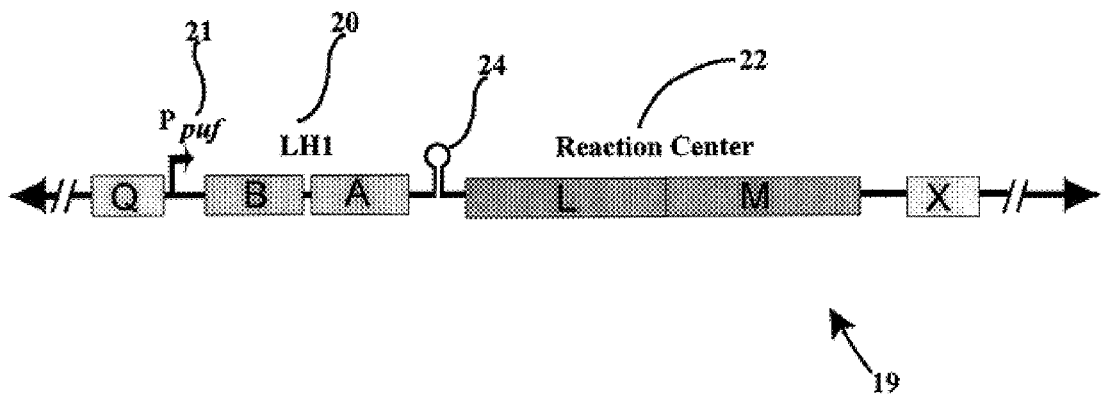
FIG. 3A is a schematic diagram of the puf operon of the Rhodobacter genus of photosynthetic bacteria for use in accordance with features of the present invention.
Figure 3B:
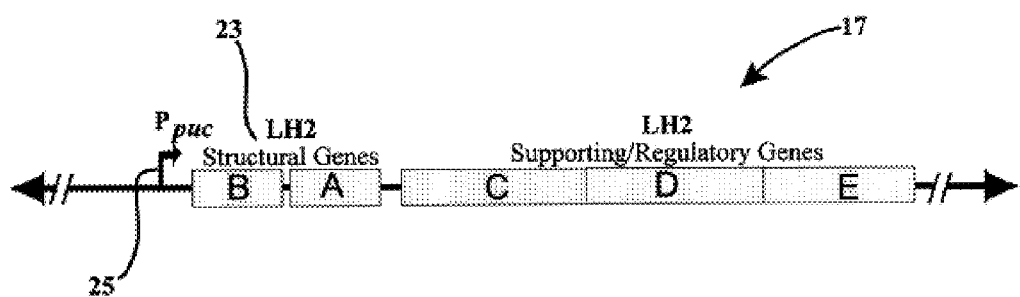
FIG. 3B is a schematic diagram of the puc operon of the Rhodobacter genus, for use in accordance with features of the present invention.

As depicted in FIG. 3A, the puf operon encodes six transmembrane proteins, specifically the two subunits of the LH1 complex 20, (the genes for the subunits represented as A and B in the drawing, respectively), the L and M subunits of the RC complex 22, and two regulatory proteins, PufQ and PufX, which are present in small amounts in the membrane. A region of stable hairpin structures 24 is located between the pufA and pufL genes. While the puc promoter for the LH2 complex is controlled by both light and oxygen, the puf promoter 21, located between pufQ and pufB, directs synthesis of RC and LH1 complex and is controlled solely by oxygen tension. At high oxygen tensions, the puf operon is repressed. When the oxygen tension is lowered, transcription of the puf operon is induced, and the transmembrane proteins that it encodes are produced in relative stoichiometries, determined in part by mRNA stability. The hairpin structure located between pufA and pufL confers this stability to varying degrees by protecting the transcript from exonuclease digestion, according to the positions of puf genes relative to its own location. Essentially, the hairpin structures serve as a means for blocking exonuclease action beyond the location of the hairpin. The result of this blocking mechanism is an increase in mRNA stability leading ultimately to production of a larger quantity of the protein of interest. The LH1-B and LH1-A proteins are present in 15–20 fold excess over the RC-L and RC-M subunits because the stable hairpin structure prevents degradation of the mRNA of the former.

All of the puf operon proteins are inserted into the developing ICM, whose synthesis is induced coordinately.

Transcription of the operon and synthesis of the ICM is induced in the lab by growing cells under semi-aerobic, chemoheterotrophic conditions in the dark per the protocols provided infra. Under these conditions, complexes of the photosynthetic apparatus are synthesized and assembled and the ICM is produced even though the cell is not using these components to grow.

Further, the inventors have found that seleno-methionine (SeMet) can be incorporated quantitatively in place of methionine in proteins of Rhodobacter. The selenium atom facilitates the determination of x-ray crystallographic phases with use of efficient multiple-wavelength anomalous dispersion (MAD) techniques at a synchrotron source. By simply slowing the shaking speed (and thus reducing the oxygen tension) at the time SeMet is added, SeMet can be selectively incorporated into proteins whose synthesis is under control of oxygen-regulated promoters. Generally, the level of oxygen in the cultures when the protein is expressed is 5–20 times lower than in repressed culture conditions, i.e., in conditions where the oxygen tension is ambient. Details of SeMet incorporation are discussed infra.

Generally, the expression system utilized herein is comprised of a host strain that carries a chromosomal deletion of puf operon, sequences, which is complemented in trans by the operon borne on a broad-host range vector. Specifically, plasmids that are used to facilitate heterologous protein expression here are modified from those vectors previously described in E. J. Bylina et al. *Plasmid* 16 175–181; and E. Takahashi, et al., Site-directed mutagenesis of *Rhodobacter spaeroides* reaction center: The role of tyrosine L222. *Current Research in Photosynthesis,* pp 169–172 (Kluwer Publ., The Netherlands, 1990), both teachings incorporated herein by reference.

Expression Vector
Construction Detail

The *R. sphaeroides* operon is cloned into a modified version of broad-host-range vector pRK404, a 10.6 kb derivative of pRK292 which carries the polylinker from pUC9 and tetracycline resistance. It is transferred to Rhodobacter via conjugation with *E. coli* donor strain S17-1; its copy number in Rhodobacter strains is 4–6/cell. Plasmid pRK404 was subsequently engineered to remove a second EcoRI site, and the HindIII site in the polylinker has also been removed to leave a single HindIII site within the puf operon. This modified vector is designated pRK404(EH).

These improvements facilitated the shuttling of singly- or multiply-mutated L and M genes in and out of the plasmid. For expression of mutant or wild-type RCs, plasmid pRKHTpuf (or a derivative of it) is used to complement, in trans, a strain of *R. sphaeroides* (ΔΔ11) that carries an engineered deletion of the chromosomal copy of this operon. The genes for the LH2 complex are also deleted in strain ΔΔ11, thus the phenotype of this strain is LH1⁻LHII⁻RC⁻. These protocols are disclosed in J. K. Lee et al. *J. Bacteriol.* 171, 3391–3405, and incorporated herein by reference.

In one scenario site-specific mutagenesis is used to append a seven-histidine tail to the C-terminus of the M subunit of RCs of *R. capsulatus*. This tail is on the periplasmic surface of the pigment-protein complex and associates readily with Ni- or Co-NTA (nitrilotriacetic acid) resin for rapid IMAC. Starting from a cell suspension, extremely pure RCs are isolated using a 4–5 hour protocol. The previous purification methodology took $\geq 3$ days and produced complexes that were markedly less pure.

Figure 5:
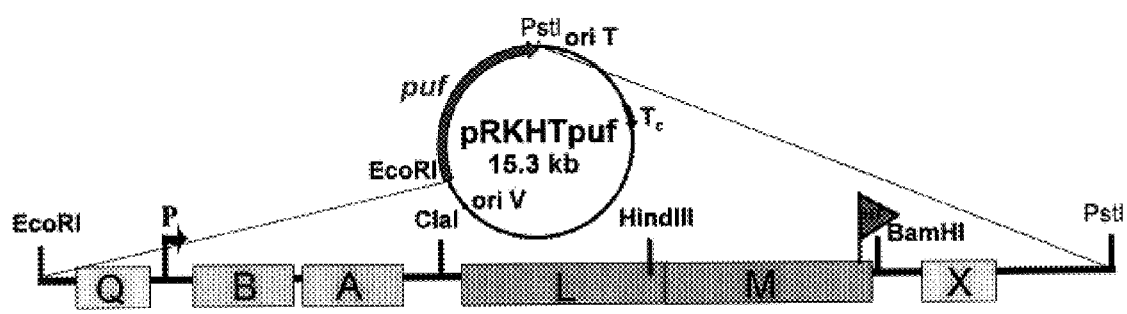
FIG. 5 is an illustration of a *Rhodobacter sphaeroides* puf operon cloned into a broad-host-range vector, in accordance with features of the present invention.

Inasmuch as the His-tag improved the *R. capsulatus* RC purification so dramatically, it was added to a vector which was invented for production of *R. sphaeroides* RCs. That vector is illustrated in FIG. 5. This improvement was especially desired for *R. sphaeroides* RCs because, unlike *R. capsulatus* RCs, the former have a greater propensity to form diffraction-quality crystals. To facilitate the addition of an analogous His-tag to this RC, an expression vector carrying a his-tagged *R. sphaeroides* M gene was obtained, as disclosed in J. O. Goldsmith, and S. G. Boxer, *Biochim. Biophys. Acta*, 1276, 171–175 (1996). In a multi-step cloning strategy, the His-tagged M gene was added to the invented *R. sphaeroides* system for site-directed mutagenesis, resulting in the vector seen in FIG. 5, discussed infra.

By coupling this expression system with the IMAC purification protocol discussed herein, large quantities of exceptionally pure RCs from both mutant and wild-type strains of *R. sphaeroides* are obtained.

A first construct used conserved restriction sites to swap the L and M genes of the *R. capsulatus* RCs for the L and M genes of the *R. sphaeroides* RCs in the updated, His-tagged plasmid pRKHTpuf. In an analogous fashion, the L and M genes of the *R. sphaeroides* RCs were used to replace their homologues in the *R. capsulatus* expression vector.

RC complexes produced in these strains are now 'hybrids' which consist of the L and M polypeptides from one species that must assemble with the endogenous H subunit produced by the host. Interspecies expression and assembly was achieved, and hybrid RC complexes purified by immobilized metal affinity chromatography (IMAC) from both organisms. Small crystals were obtained from hybrid RCs produced in the *R. capsulatus* expression system (L and M subunits from *R. sphaeroides*+H subunit of *R. capsulatus*).

Figure 4:
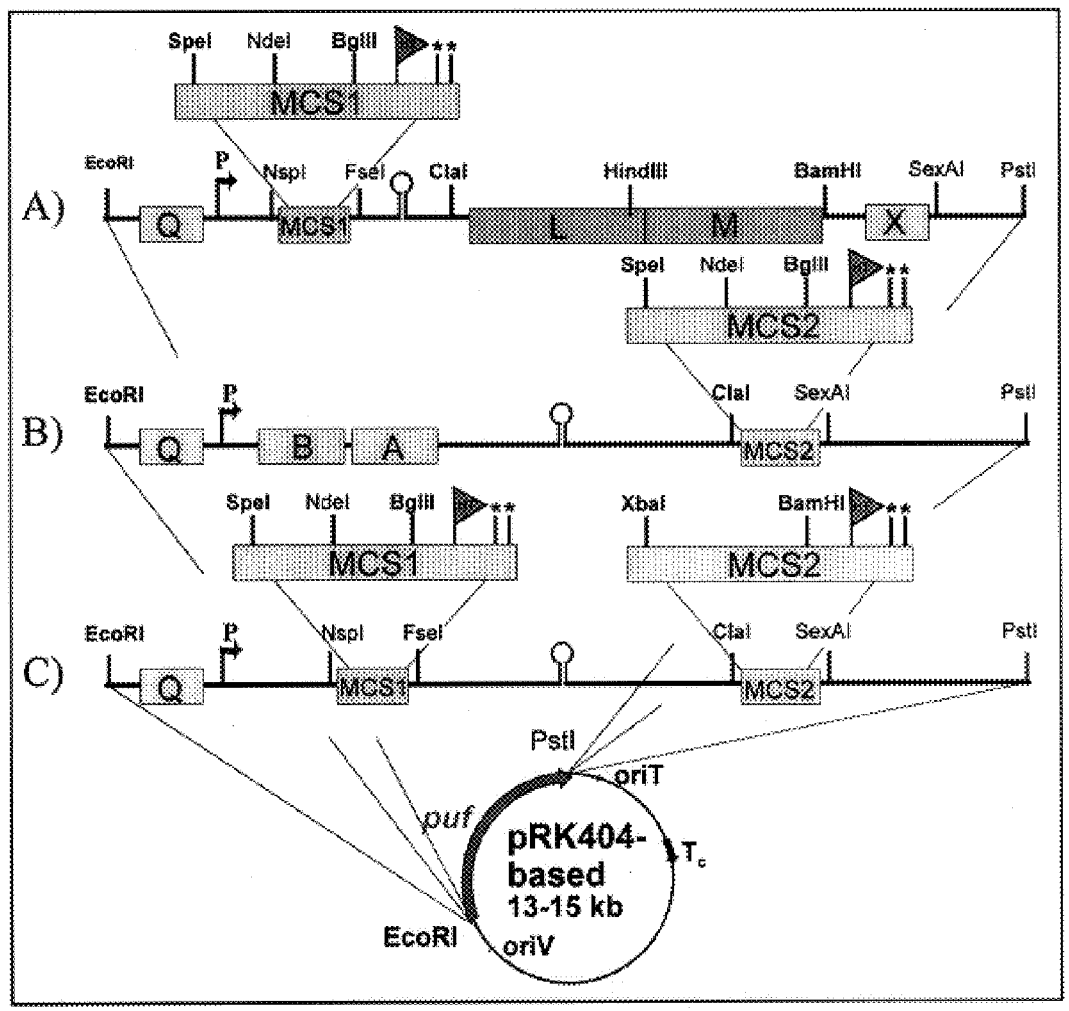
FIG. 4 is a schematic diagram of genes and restriction endonuclease sites of expression vectors for use in Rhodobacter.

FIG. 4 is a diagram of inventor-engineered expression vectors for use in *R. sphaeroides*. These engineered vectors are designed to place expression of a foreign gene under control of the oxygen-regulated puf operon promoter (P). The position of the gene relative to the region of stable hairpin structure in the operon dictates the relative level of expression. A multiple cloning site (MCS) replaces genes of the LH1 complex (B and A) in Vector A for high-level expression of the foreign protein. Vector B allows for insertion of the foreign gene in place of reaction center genes (L and M) at MCS2 for a moderate expression level. Dual expression of two genes is possible with Vector C.

Figure 14:
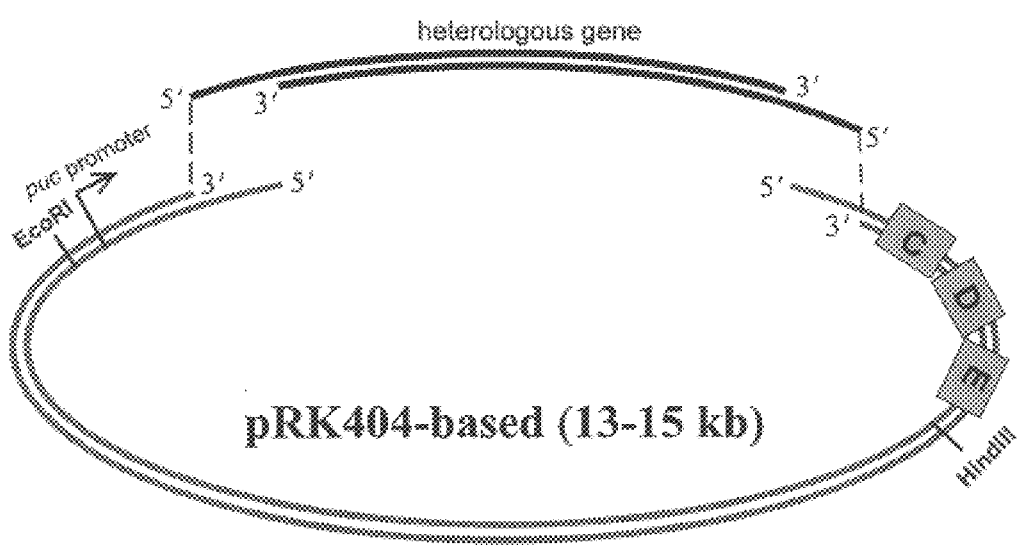
FIG. 14 is an illustration of a vector based on the puc operon for ligation independent cloning and the expression of heterologous proteins in Rhodobacter.

Other broad-host-range vectors, host-specific vectors, or vectors utilizing ligation independent cloning (LIC) strategies are also appropriate vehicles to facilitate protein expression in trans. For example, FIG. 14 depicts a vector based upon the puc operon and the broad-hostrange vector pRK404. LIC protocols utilize the proof-reading capabilities of modern polymerases to generate lengthy complementary cohesive ends between the insert and vector which when annealed in the absence of ligating enzymes successfully transform organisms with high efficiency. Conjugation is utilized to shuttle LIC clones into Rhodobacter. A more thorough disclosure of LIC is found in C. Aslanidis et al, *Acids Res.* 18, 6069–6074, and incorporated herein by reference.

Aside from ΔΔ11, publically available through Argonne National Laboratory, Argonne, Ill., other hosts containing a partial to a full complement of the proteins of the full photosynthetic membrane are also suitable. Such suitable hosts include, but are not limited to the following *R. sphaeroides* organisms:

1. ATCC #17023.
2. PUC705-BA, which is a strain publically available and disclosed in Lee et al., referenced supra. This is an LH2-deletion strain.
3. LMX21, which is a strain publically available and disclosed in J. W. Farchaus, and D. Oesterhelt, *EMBO Journal* 8, 47–54. This strain is deleted for pufL, pufM and pufX.
4. LH2-containing, LH1- and RC-deleted strains.

The equivalent to *R. sphaeroides* ΔΔ11 in *R. capsulatus* is strain U43, publically available and disclosed in D. C. Youvan et al, (1985) *Gene*, 33, 19–30. This strain does not make LH2 due to a point mutation and is deleted for most puf operon genes. Aside from U43, other suitable *R. capsulatus* hosts include, but are not limited to, the following:

1. ATCC 11166.
2. U34, publically available through Youvan et al. This strain does not make LH2 due to an engineered deletion. The puf operon is present.
3. U15, also publically available through Youvan et al. This strain has LH2 and is deleted for most puf operon genes.
4. LH2-containing, LH1- and RC-deleted strains.

Protein Separation
Protocol Detail

To simplify and improve the purification process associated with isolating the generated proteins, a suitable moiety with an affinity for a predetermined structure is appended to the generated protein for subsequent separation. The inventors have determined that the His-tag is of extreme utility in improving the ability to purify and manipulate RCs for functional studies. A polyhistidine tail (HT) is inserted in frame at the C-terminus of the MCS before stop codons (*) which terminate protein translation. This HT will expedite purification of the expressed protein. The histidine tag also can be attached to the N-terminus. Other tags also are appropriate, including, but not limited to intein, maltose binding protein, and small peptide tags with high-affinity antibody-based recovery systems. A myriad of suitable peptide tags are commercially available, including, but not limited to, E-tag™ of Amersham Pharmacia Biotech, Inc. of Piscataway, N.J., and the S-tag™ of Novagen, Inc., Madison, Wis. Any of the attached tags can be designed to be cleaved with a compatible protease.

The poly-histidine tail confers many other advantages to the *R. capsulatus* expression system. One of the more useful is that the His-tag facilitates the use of different surfactants with a wider range of properties to remove the complex from its native membrane environment. For example, the inventors have found that when IMAC protocols are used in combination with a mild charged detergent (which is incompatible with traditional ion exchange chromatography), the cofactors of the resulting product remain in their native states as evidenced by spectral properties--dimeric bacteriochlorophyll in R. capsulatus RCs absorbs at its native 870 nanometer position versus a shift to 850 nm when other detergents are utilized. Small crystals of His-tagged RCs of R. capsulatus were obtained.

IMAC was also used to isolate LH1/RC superassemblies in large quantity for crystallization trials. The non-covalent association between the RC and LH1 is strong enough to allow purification of the entire superassembly utilizing the single poly-histidine tail on the RC. Crystals of the superassembly were obtained.

The His tag also enables the changing of surfactants after removal of the complex from the native lipid bilayer. These purification advantages do not come at the expense of the functional or structural integrity of the complex. In fact, four different types of spectroscopic experiments that measure electron transfer, proton transfer, or energy transfer reactions in the RC have indicated that the poly-histidine tag does not interfere with the normal functions of the complex.

The inventors' protocol for purifying the multi-subunit RC and the LH1/RC superassembly complexes with a single his-tag was adapted to exploit the Rhodobacter heterologous expression system to co-purify proteins which are members of larger membrane complexes. This adaptation requires and enables the simultaneous expression of interacting proteins. It is based on the observation that genes for many proteins that associate into functional complexes, are organized into conserved DNA segments. The ability to express clusters of mutually dependent proteins enables methods in which systematic co-expression of two or more membrane-associated proteins results in successful production of proteins and/or complexes heretofore recalcitrant to efforts of mono-molecular expression.

Coordinated expression of multiple genes is accomplished by shuttling a gene cluster, containing one gene that is affinity tagged (such as with histidine), into one of the above Rhodobacter expression plasmids. If the members of the cluster physically interact, the single protein which is affinity tagged will facilitate purification of the entire complex, thereby allowing for the identity of proteins which associate to form a functional multi-subunit macromolecular membrane-associated machine. FIG. 4C depicts a vector that is designed for the tandem expression of two genes whose protein products associate in a stoichiometry other than 1:1.

While the above disclosed protocol dealt with single affinity tags, multiple affinity tags, or other types of affinity tags also are suitable and enabled with this protocol. Multiple affinity tags serve to enhance purification of the target protein and certain other moieties.

SeMet Incorporation Detail

The inventors utilize MAD techniques for the determination of de novo x-ray structures. With MAD, experimental phases are obtained from small changes in x-ray diffraction patterns acquired using incident wavelengths that are chosen to be far from, near, and at the absorption edge for the particular anomalous scattering atom. Monochromatic radiation from a synchrotron source is imperative for these experiments.

The incorporation of a selenium atom in the protein crystal is one way to provide an anomalous scatterer as a key to solving crystal structure by MAD techniques. Selenium may be incorporated into a protein sequence by use of the amino acid analog seleno-methionine (SeMet) during biosynthesis of the polypeptide chain. These techniques have been used successfully for some proteins derived from E. coli, and have also been used with Chinese hamster ovary cells, as disclosed in S. Doublie, Methods in Enzymology, pp 523–530 (Academic Press, New York, 1997), and incorporated herein by reference. The inventors have developed methods for similar substitution of methionine by SeMet in two species of Rhodobacter.

Briefly, cells were grown to late log phase in minimal medium (RCV for R. capsulatus and minimal R26 plus vitamins for R. sphaeroides), the media described respectively in Weaver et al., Arch. Microbiol. 105, pp. 207–216; and Gerhardt, et al., Methods for General and Molecular Bacteriology p. 664 (American Society for Microbiology, Washington, D.C. 1994), and incorporated herein by reference. These media were prepared containing the appropriate antibiotics, and maintained at routine shaker speeds for moderate aeration of the culture.

The cells were then diluted 1:250 into fresh medium, antibiotics, and vitamins and were grown to mid-log phase under conditions of high oxygen tension which repress expression of proteins under the control of the puf promoter and production of the ICM. High oxygen tension is achieved by placing 500 ml of culture into a 2.8 L Fernbach flask shaking at 320 rpm for R. sphaeroides and 350 rpm for R. capsulatus at temperatures between 32 and 34° C. Cultures of both species remain essentially "colorless"/non-pigmented under these conditions, although R. capsulatus tends to appear slightly more pigmented at this stage than R. sphaeroides depending upon the length of time the cells spend under these conditions. Optimally, for efficient incorporation of SeMet, pigment expression, puf promotion, and ICM production should be repressed.

Once the cultures reached mid-log phase, an amino acid cocktail which inhibits the synthesis of methionine in prokaryotes was rapidly added to the culture. The cells were allowed to continue to grow at high oxygen tension for one hour following the addition of the cocktail to consume any residual methionine. Then, 60 mg/L of L-SeMet or 120 mg/L of DL-SeMet was added to the culture flask of either species at the same time that the oxygen tension was lowered by reduction of the shaking speed to 80 rpm. R. capsulatus cultures required a supplementary addition of S-adenosyl-L-methionine (SAM; a methionine derivative that is a known intermediate in bacteriochlorophyll biosynthesis in these organisms) at this stage due to the "toxic" effects of SeMet and/or methionine deprivation in this species. Cultures of both organisms were then grown overnight and harvested the following morning, showing only marginal increases in cell density. However, the cells were remarkably pigmented (indicating ICM synthesis); ICM was then harvested and ICM protein was purified.

The expression of ICM proteins of the photosynthetic apparatus under these conditions is between 10 and 40% of the expression of the same protein in the control flasks with L-met added instead of SeMet (or SeMet+SAM). However, the level of expression in the L-Met control culture is only 30% of that attained under normal growth/induction conditions encountered by the inventors.

RC protein was isolated from SeMet-labeled and control (L-met labeled) cultures of R. sphaeroides and R. capsulatus for amino acid analysis. The results of the analyses revealed that the adapted culture protocols outlined above result in nearly quantitative (100 percent) incorporation of SeMet in R. sphaeroides RC protein and up to 82 percent incorporation of SeMet in R. capsulatus RC protein. These results represent one of the first reports of the successful incorporation of SeMet into an overexpressed membrane protein of a prokaryote.

Proteins from any number of genomic sources, including human, can be induced and inserted into a developing ICM.

EXAMPLE 1
Aequorea Green
Fluorescent Protein

For this example, the inventors introduced Aequorea Green Fluorescent Protein (GFP), which is a jelly-fish-derived bioluminescent, as an easily quantifiable soluble reporter gene product into the R. sphaeroides expression system. The gene was obtained from Quantum Biotechnologies, Inc. in Montreal. Standard manipulation protocols were employed, such as that discussed supra.

The GFP gene was cloned into two different places in the puf operon to test expression levels that could be obtained by placing the gene either before or after the stable hairpin structures described above. In the first construct, the GFP gene replaced the pufB and pufA genes of the β and α subunits of LH1.

In the second construct, the GFP gene replaced the pufL and pufM genes (L and M subunits) of the RC. Directional cloning of the GFP gene via flanking ClaI and BamHI restriction sites was used to replace the RC genes. To engineer the switch for the LH1 genes, a synthetic multiple cloning site (MCS) insert containing NspI, SpeI, BglII, and FseI restriction sites was first swapped for a NspI/FseI fragment in the puf operon. The GFP gene was then directionally cloned into the SpeI/BglII sites in the MCS region as an XbaI/BamHI fragment.

These constructs were conjugated into R. sphaeroides. The strains were grown in large scale culture in 2.8 L Fernbach flasks containing 2 L of YCC medium containing tetracycline. Depending upon the size of the inoculum, the cultures were grown for up to 3 days at 125 rpm in a floor model Lab-Line shaker. Cells were harvested and GFP compartmentalization and expression levels were measured via cell fractionation and UV-vis absorption spectroscopy of resulting supernatants or resuspensions of pelleted material. The GFP content of cell extracts was easily quantified because the spectra of the compartments containing GFP revealed intense new bands in the visible spectrum which do not overlap with others inherent in Rhodobacter.

The cell fractionation experiments revealed that the soluble GFP accumulated in the cytoplasm in all constructs. Its location was readily identifiable by the naked eye due to its color. Using an extinction coefficient of 26,200 cm$^{-1}$M$^{-1}$ and a molecular weight of 28,000 (as reported in the Quantum Biotechnologies applications manual for autofluorescent proteins), the inventors conservatively estimate that the Rhodobacter system is capable of producing at least 45 mg of this protein per L of culture.

Surprisingly and unexpectedly, the inventors found that heterologous expression was enhanced (approximately threefold) when the GFP gene was inserted in place of the RC genes rather than when the GFP gene replaced the LH1 genes. The inventors surmise that removal of the RC sequence is concomitant with removal of endonuclease sites located therein. Alternatively, construction of the expression plasmids could serve as a means to modify the intergenic hairpin region (found between the LH1 and RC genes) which normally hinders the activity of exonucleases.

Figure 6:
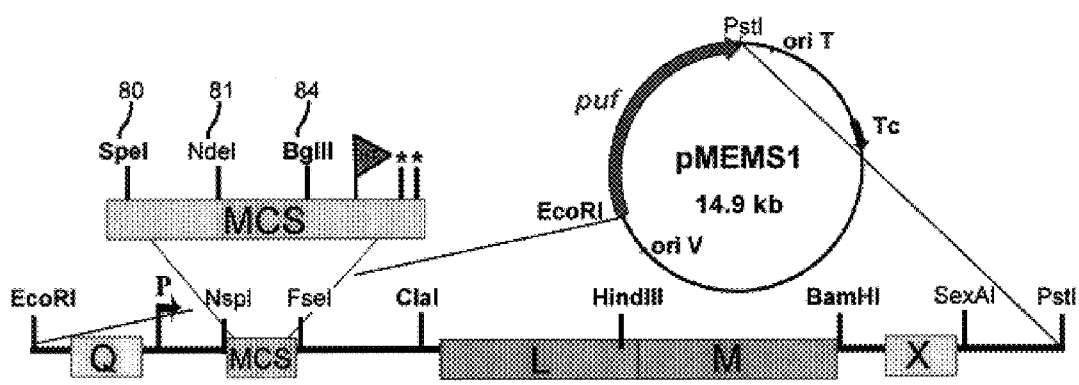
FIG. 6 is an illustration of an *R. sphaeroides* operon for expression of heterologous genes in place of light-harvesting antennae genes, in accordance with features of the present invention.

To facilitate cloning of non-homologous or non-related heterologous membrane proteins, the inventors engineered a multiple cloning site in place of R. sphaeroides antenna genes. The resulting platform vectors contain restriction sites which are unique in both pRK404 and the R. sphaeroides operon. These restriction sites also are compatible with commercially-available expression vectors, such as the pET series of expression vectors from Novagen, the pGEM series from Promega, and the pBluescript series from Stratagene. Lastly, these genes carry histidine tags. An oligonucleotide adapter was synthesized carrying NspI and FseI cohesive ends which were used to replace the NspI/FseI section of the puf operon containing the pufB and pufA genes. The enzymes included in the MCS are SpeI (compatible with XbaI, NheI, StyI and AvrII cohesive ends), NdeI, and BglII (compatible with BamHI). Three versions of these types of constructs (diagramed in FIGS. 4A and 6) were engineered for use in linking the 3' end of any cloned gene with the seven member His-tag and a set of two stop codons in the proper reading frame. The MCS and HT regions designate the multiple cloning site and histidine tag site, respectively. OriV connotes the replication origin for E. coli. OriT designates the broad host origin. ** designates stop codons in the proper reading frame.

EXAMPLE 2
Expression of Human
Membrane Protein

The inventors produced a vector, containing R. sphaeroides puf operon, to facilitate replacement of light-harvesting antennae genes with genes of heterologous protein. A well characterized protein whose structure is still unknown was selected. Several clones of voltage-dependent anion channels (VDACs) were identified. These mitochondrial porin-like channels cannot be modeled effectively by using the known bacterial porin structures. HVDAC1 gene from Homo sapiens, cloned in a general E. coli cloning vector, pBS$^-$ (Stratagene, Inc.) was obtained from Dr. Michael Forte, at Oregon Health Sciences University (Portland, Oreg.).

The gene was subsequently amplified by high-fidelity PCR (using the Pfu-Turbo polymerase, Stratagene, Inc.) with ends designed to be compatible with the R. sphaeroides heterologous platform vector (pMEMS1). After amplification and restriction enzyme digestion, the PCR product carried SpeI and BamHI cohesive ends and no intrinsic stop codon. Upon insertion into pMEMS1 (via directional cloning into the SpeI and BglII compatible ends), translational termination and the affinity tag are, by design, provided in frame by sequences 3' to the BglII site in the platform vector depicted in FIG. 6. The pMEMS1 is constructed using the broad-host-range vector pRK404.

Figure 7:
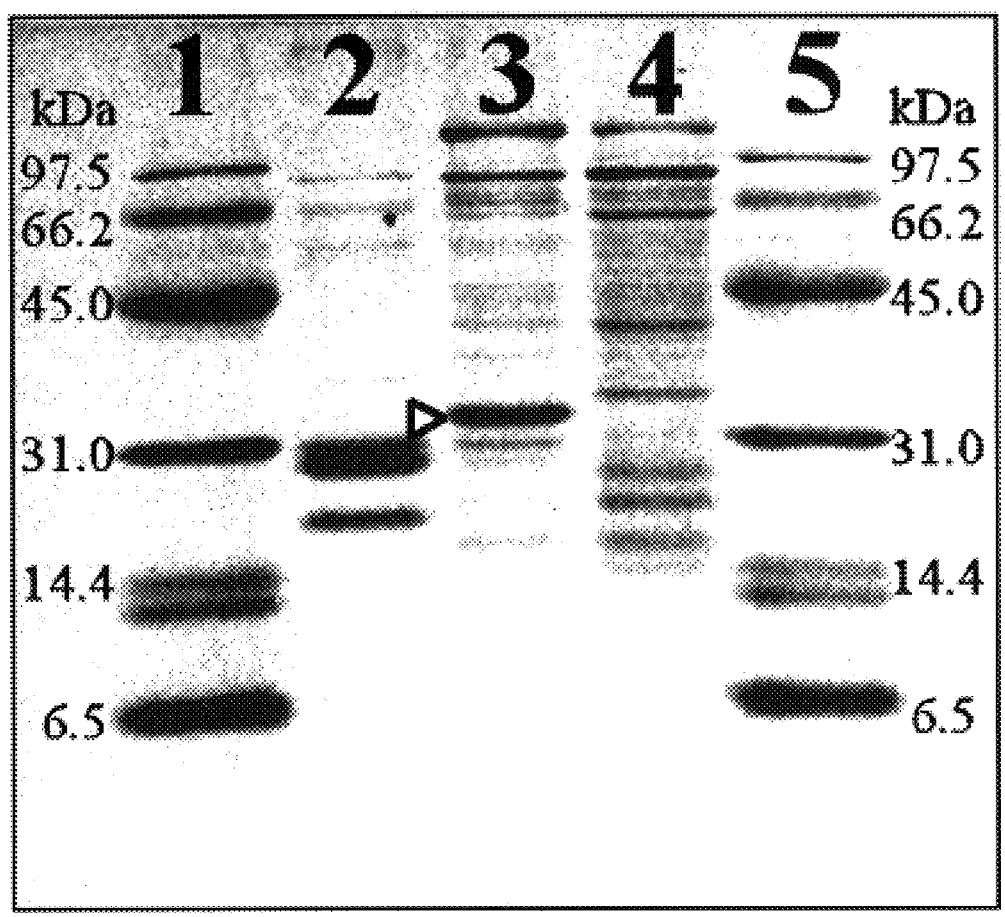
FIG. 7 is a depiction of a protein gel depicting overexpression of a transmembrane *H. sapiens* protein, in accordance with features of the present invention.

After conjugation of the new construct into R. sphaeroides and large scale culture of the resulting transconjugants, solubilized cytoplasmic and ICM-fractions were subjected to IMAC. FIG. 7 shows an SDS-PAGE gel of proteins that bound to the column. FIG. 7 depicts a Coomassie blue stained 12.5 percent acrylamide gel showing overexpression of a transmembrane H. sapiens voltage dependent anion channel in the intracytoplasmic membrane fraction of Rhodobacter. Lanes 1 and 5 are molecular weight markers. Lane 2 is a control sample of purified reaction centers showing the L, M, and H subunits. Lane 3 is the membrane fraction showing the HVDAC. Lane 4 is the soluble fraction from the same cells. Proteins in Lanes 2–4 were purified by IMAC, described supra.

The results reveal a prominent ~32 kilo-Dalton (kDa) band in the ICM-fraction from cells harboring the HVDAC constructs. The size of this band matches that predicted; the band is completely absent in the soluble fraction. Thus, this result represents successful expression of a heterologous membrane protein in Rhodobacter and its incorporation into the ICM. Since both the human HVDAC and jellyfish GFP genes were well expressed, codon usage does not appear to present a problem for expression of eukaryotic sequences in prokaryotic Rhodobacter. In the event that rare codons inhibit the expression of a candidate protein in Rhodobacter, the coding sequence of the protein is manipulated to eliminate those problem codons. Alternatively, or in addition, genes that encode rate tRNAs for co-expression with the candidate are introduced.

These results confirm the potential of this Rhodobacter system for the expression and purification of functional membrane proteins from any organism.

Figure 8:
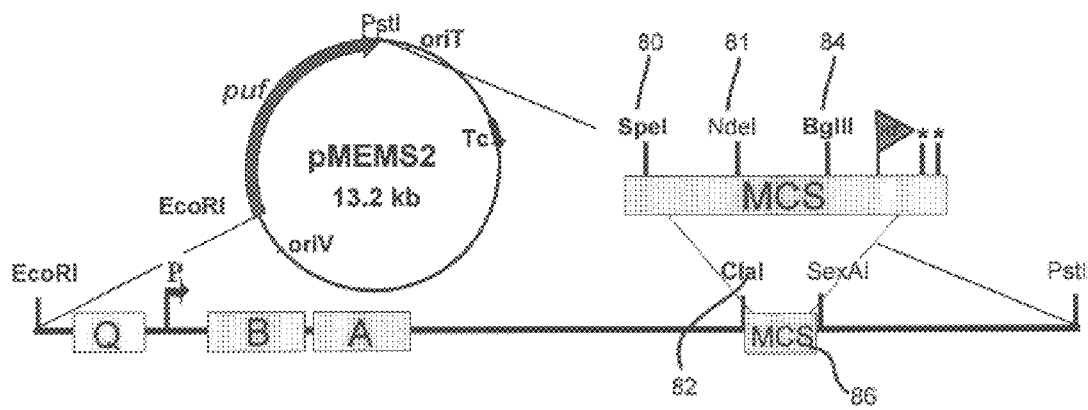
FIG. 8 is an illustration of an *R. sphaeroides* plasmid for expression of heterologous genes in place of reaction center genes, in accordance with features of the present invention.

Generally, the inventors believe that their *R. sphaeroides*-based heterologous expression system will yield higher levels of heterologous membrane protein expression if foreign genes are located in place of the RC genes in the operon, as depicted in FIG. 8, which shows an *R. sphaeroides* plasmid for expression of heterologous genes in place of RC L and M genes. Restriction sites for SpeI (element 80), ClaI (element 82), and BglII (element 84) are unique in this plasmid.

For insertion of a multiple cloning site (MCS) in this location, a ClaI/SexAI fragment, 86, carrying the pufL, pufM and pufX genes from the *R. sphaeroides* operon (FIG. 6) is replaced by a double-stranded DNA cartridge that carries multiple cloning sites with compatible cohesive ends. The same three restriction sites, i.e., SpeI 80, NdeI 81, and BglII 84, found in the MCS that replaces the pufB and pufA genes (FIG. 5) are incorporated in the MCS used to replace the RC pufL and pufM genes. Optionally, a stable structure hairpin following the stop codons in this region of the operon is inserted as protection against exonuclease degradation, thus improving transcript stability.

As with *R. sphaeroides* and as noted supra, the inventors envision utilizing *R. capsulatus* as a host for expression of foreign genes. Cultures of this species grow faster, reach higher cell densities, are more amenable to a variety of media and culture conditions, and the sequence of its genome is nearly complete.

Figure 9:
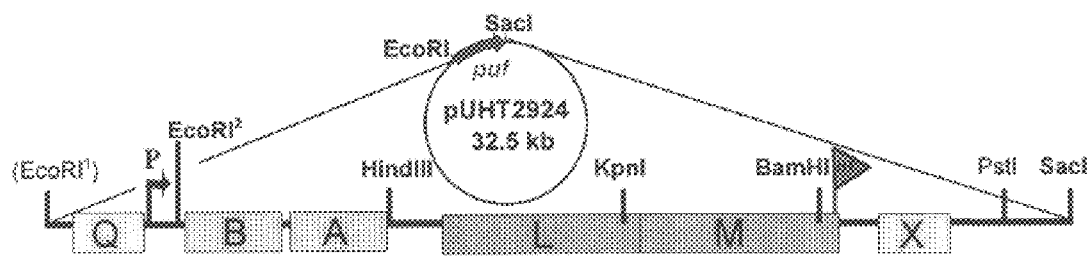
FIG. 9 is an illustration of an *R. capsulatus* puf operon residing in a broad-host-range vector, in accordance with features of the present invention.

The *R. capsulatus* system is based upon the pU2924 vector disclosed in Bylina et al., *Plasmid*, 16, 175–181 (1986) and *Bio/Technology*, 7, 69–74 (1989), and incorporated herein by reference. The puf operon contained within this vector is diagramed in FIG. 9. Plasmid pU2924 is based on broad-host-range vector pRK292, and carries genes for resistance to ampicillin, tetracycline, and kanamycin.

The inventors' strategy for expression of foreign genes in *R. capsulatus* is similar to that used for *R. sphaeroides*, discussed supra. Multiple cloning sites replace the functional photosynthetic genes in the *R. capsulatus* puf operon. To make cloning and screening easier, the *R. capsulatus* operon is first transferred from the large pU2924 vector to the pRK404(EH) vector inasmuch as the smaller pRK404 is much likelier to have unique restriction sites. The operon is moved from pU2924 into the EcoRI/PstI sites of pRK404 in a two-step procedure. First, the EcoRI$^2$/PstI fragment is introduced into pRK404(EH) to form an intermediate construct. This plasmid lacks the puf promoter, thus the upstream sequence between EcoRI$^1$ and EcoRI$^2$ is required, inasmuch as the promoter in that fragment has to be appended to the promoter-less construct. The (EcoRI$^1$)-EcoRI$^2$ sequence from the *R. capsulatus* operon is amplified with PCR, using the oligonucleotide primer to change the (EcoRI$^1$) sequence into an ApoI site which has ends that are compatible with EcoRI. This fragment is then cloned into the EcoRI-digested intermediate. The resultant plasmid houses all the necessary machinery for expression of the *R. capsulatus* puf operon in the pRK404 vector. This plasmid has a single EcoRI site since the ligation of an ApoI end with an EcoRI end results in the loss of the EcoRI recognition sequence. The unique EcoRI is important in the strategy for introduction of the multiple cloning site in place of the pufB and pufA genes.

Figure 10:
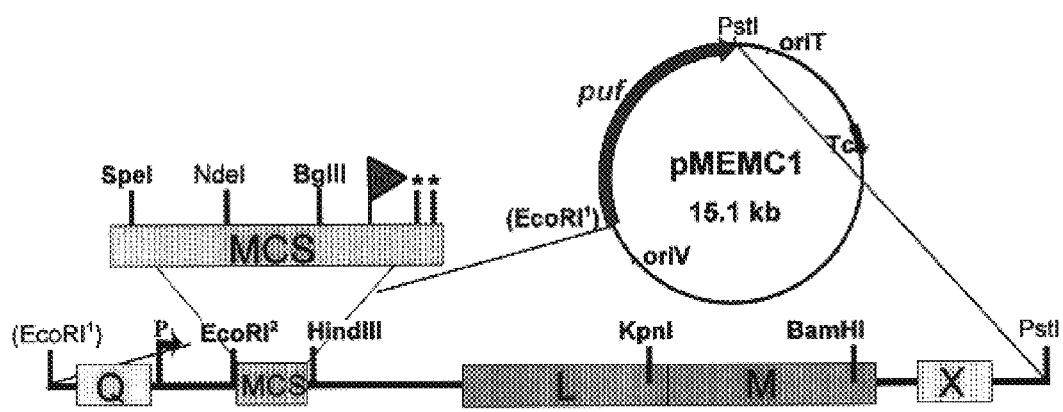
FIG. 10 is an illustration of an *R. capsulatus* plasmid for expression of heterologous genes in place of light-harvesting antennae genes, in accordance with features of the present invention.

FIG. 10 is an illustration of an *R. capsulatus* plasmid utilized to facilitate the insertion of genes for heterologous proteins in the place of LH1 antennae genes. Specifically, to introduce the multiple cloning site in place of LH1 genes, the EcoRI$^2$-HindIII fragment from the operon is replaced with a double-stranded DNA cassette which carries SpeI, NdeI, and BglII as the restriction sites in the multiple cloning region, as depicted in FIG. 10.

Figure 11:
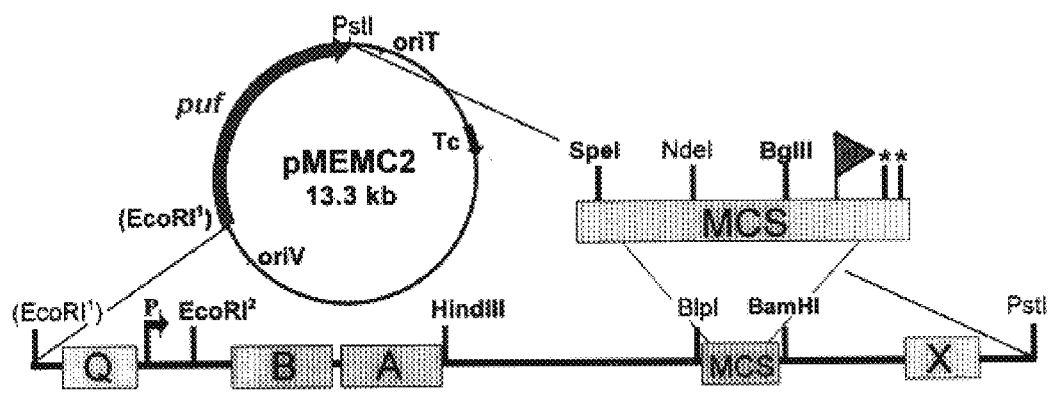
FIG. 11 is an illustration of an *R. capsulatus* plasmid for expression of heterologous genes in place of reaction center genes, in accordance with features of the present invention.

FIG. 11 is an illustration of an *R. capsulatus* plasmid utilized to facilitate insertion of genes coding for heterologous proteins in the place of reaction center genes. To introduce an MCS in place of the RC genes, the BlpI-BamHI fragment is swapped for a cassette with compatible ends. Again, the cassette will carry the SpeI, NdeI, and BglII sites which are compatible with other plasmids of the pMEM series, yielding pMEMC2, so depicted in FIG. 11.

His-tagged RC
Fusion Detail

The inventors have developed a system for the expression and purification of soluble proteins. The soluble proteins are tethered to autologous His-tagged, ICM-bound membrane proteins via a peptide linker. This linker incorporates a site for proteolytic cleavage of the fusion protein into its two component parts by thrombin. The construct fuses the His-tagged *R. sphaeroides* RC to a soluble GFP through this thrombin-cleavable linkage. Other constructs are suitable, including those which a) tether the soluble protein to any other stable membrane protein, b) include other cleavable sites, or c) utilize ligation-independent-cloning protocols. To make the test plasmid, the His-tagged M gene of *R. sphaeroides* is amplified using PCR such that the natural stop codon is removed. Linkage to the GFP will be provided via the BamHI site at the end of the *R. sphaeroides* M gene. The linker containing a thrombin cleavage site is added to primers for use to amplify the GFP with PCR. These primers also add a BglII site on the 5'-end and a BamHI site on the 3'-end.

Figure 12:
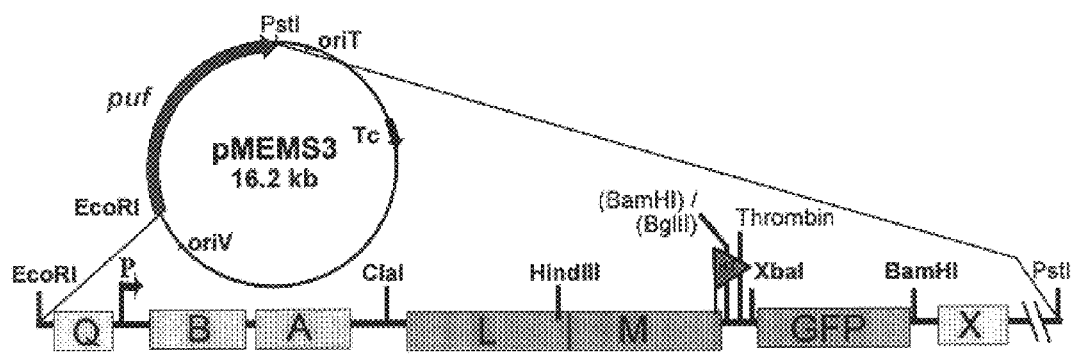
FIG. 12 is an illustration of an *R. sphaeroides* plasmid for the expression of soluble protein tethered to membrane protein, in accordance with features of the present invention.

Plasmid pMEMS3 (FIG. 12) is constructed through an intermediate in which the reengineered M gene is swapped for the wild-type M gene using directional cloning with HindIII and BamHI. Subsequently, the BamHI-digested intermediate will be ligated with a BglII/BamHI-digested PCR fragment carrying the reengineered GFP. This test construct is designed to enable efficient swapping of the GFP for other soluble targets in the future via the unique XbaI and BamHI flanking sites.

Figure 13:
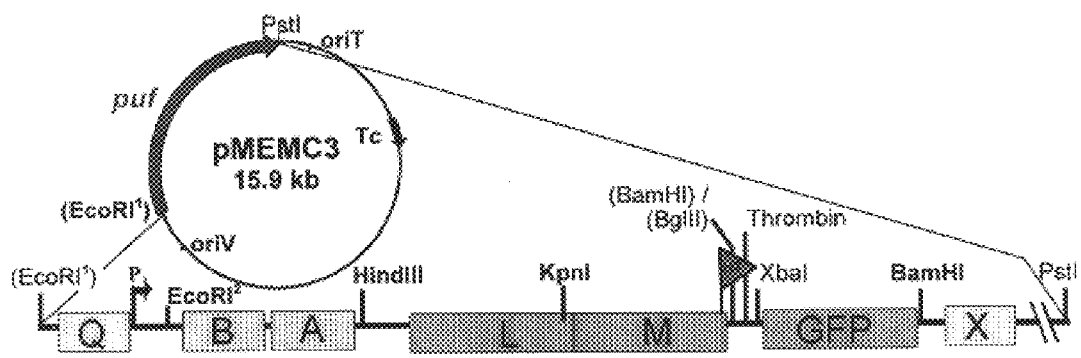
FIG. 13 is an illustration of an *R. capsulatus* plasmid for the expression of a soluble protein tethered to a membrane protein; in accordance with features of the present invention.

A similar strategy is utilized to construct an *R. capsulatus* plasmid for expression of soluble protein with a His-tagged membrane protein tether. That plasmid is depicted in FIG. 13.

rec A Mutant
Protein Detail

The RecA protein of many bacteria catalyzes the pairing of a single-stranded DNA molecule with a complementary region of a duplex DNA molecule, and the ATP-dependent displacement of the other strand of the duplex. This strand assimilation reaction promotes the exchange of information by homologous recombination. In strains carrying mutations of the recA locus, the sensitivity to UV irradiation is much greater and frequencies of homologous recombination are much lower in strains. Thus, a recA mutation is a common feature of bacterial strains that are used as general hosts for cloning of foreign genes.

Interposon mutagenesis can be used to construct recA strains of R. capsulatus and R. sphaeroides as one of the steps towards making these species useful hosts for the cloning, maintenance, and high-level expression of heterologous genes.

To construct the mutant strain of each species, the recA gene is isolated from chromosomal DNA and cloned. The sequences of the recA genes are known for both R. capsulatus and R. sphaeroides. As such, the design of oligonucleotides for amplification of the gene from chromosomal DNA by use of the polymerase chain reaction (PCR) is readily accomplished. The PCR product is then cloned into a 'suicide' vector (e.g., pSUP202, tet$^R$) which can be maintained in E. coli but is incapable of replication in Rhodobacter. The majority of the recA coding region is then excised and replaced with an interposon encoding antibiotic resistance. In addition to tetracycline resistance (which will already be encoded by pRK404 vector sequences in the expression constructs), genes for resistance to kanamycin, and spectinomycin work well in Rhodobacter.

Flanking recA sequences of 500–1000 bp are left on either side of the inserted antibiotic resistance gene to facilitate recombination between interrupted recA gene of the plasmid and the homologous chromosomal sequences. The suicide vector containing the interrupted recA gene is then returned to the host strain of Rhodobacter by conjugation from E. coli donor strain S17-1.

Exconjugants resulting from double crossover events, in which the gene interruption has replaced the chromosomal copy of the recA gene, are identified by selection for resistance to the antibiotic encoded by the interposon sequence, and sensitivity to tetracycline. Any exconjugants that are still resistant to tetracycline will be excluded as single crossovers in which the chromosomal DNA carries both the wild copy and the interrupted copy of the recA gene.

Following the identification of putative exconjugants, deletion of the recA gene is confirmed by Southern hybridizations that indicate: a) presence of sequences for the interposon in chromosomal DNA; b) a change in the size of chromosomal DNA fragments that hybridize to DNA probes derived from recA flanking sequences; and c) the absence of hybridization signals when sequences derived from the interior (deleted region) of the recA gene are used as probes. In addition, the candidate deletion strains are tested for their sensitivity to UV irradiation.

Figure 15:
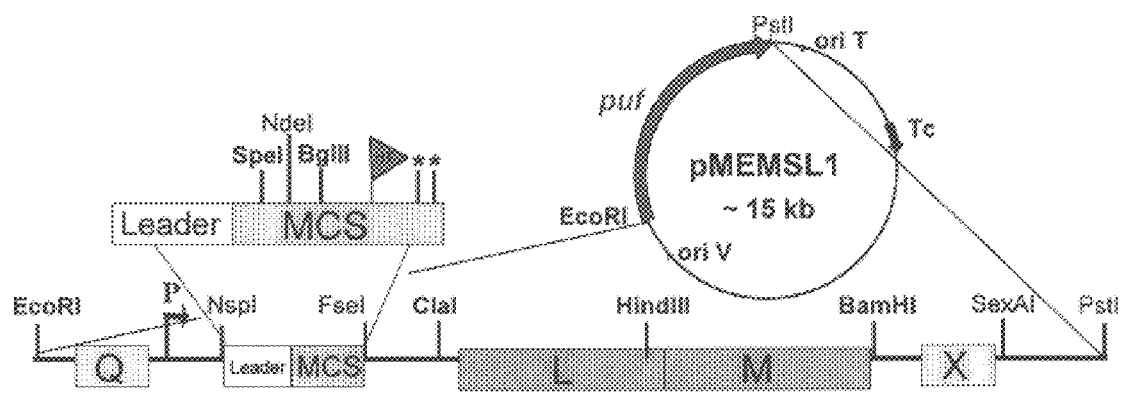
FIG. 15 is an illustration of a plasmid for expression of a heterologous gene fused to a leader sequence in Rhodobacter, in accordance with features of the present invention.

While the invention has been described with reference to details of the illustrated embodiment, these details are not intended to limit the scope of the invention as defined in the appended claims. For example, FIG. 15 depicts a vector for the expression of fusion proteins in Rhodobacter. In this scenario, a sequence of DNA from native open reading frames of the puf or puc operons is fused in frame to genes encoding heterologous membrane proteins. When translated, the fusion constructs produce peptides which are more readily inserted and are discretely targeted to the developing ICM. The lengths of the leader sequences would range from between approximately 15 and 105 base pairs to result in leader peptides of between 5 and 35 amino acids. As discussed supra, heterologous gene inserts are engineered to incorporate necessary features for purification, transcript stability, and targeting.

What is claim is:

1. A method for expressing heterologous protein in Rhodobacter species, said method comprising producing and sequestering the protein within an inducible Rhodobacter intracytoplasmic membrane system, wherein the protein and membrane are produced simultaneously.

2. The method as recited in claim 1 wherein the protein contains an affinity tag.

3. The method as recited in claim 1 wherein the protein is a complex of mutually co-dependent proteins.

4. The method as recited in claim 1 wherein the expression of the heterologous protein and the inducible membrane system depend from the same environmental stimuli.

5. The method as recited in claim 1 wherein the environmental stimuli actual the puf promoter from the Rhodobacter genus.

6. The method as recited in claim 1 wherein the environmental stimuli actuate the puc promoter from the Rhodobacter genus.

7. The method as recited in claim 1 wherein the coding sequence for the heterologous protein contains the puf operon of the Rhodobacter genus.

8. The method as recited in claim 1 wherein the coding sequence for the heterologous protein contains the puc operon of the Rhodobacter genus.

9. The method as recited in claim 3 wherein the inducible membrane system is controlled by the same environmental stimuli which induce expression of the puf promoter or the puc promoter of the Rhodobacter genus.

10. The method as recited in claim 4 wherein the environmental stimuli are stimuli selected from the group consisting of oxygen tension and light.

11. A method for producing and sequestering a functional protein within the Rhodobacter intracytoplasmic membrane wherein the expression of the membrane protein is under control of a Rhodobacter inducible promoter and wherein the functional protein is synthesized at the same time the sequestering membrane is synthesized, the method comprising:

a) supplying a DNA sequence containing the code for the membrane protein, the functional protein, a promoter for the functional protein, and the Rhodobacter inducible promoter, wherein the promoter for the functional protein and the Rhodobacter inducible promoter are actuated by the same environmental cue; and b) subjecting the functional protein promoter and the Rhodobacter inducible promoter to the environmental cue.

12. The method as recited in claim 11 wherein the production and sequestering of the functional protein is regulated by the puf promoter or the puc promoter of the Rhodobacter genus.

13. The method as recited in claim 11, wherein the protein contains an affinity tag.

14. The method as recited in claim 11 wherein the intracytoplasmic membrane is regulated by the same environmental stimuli which induce expression of the puf promoter of the Rhodobacter genus.

15. The method as recited in claim 11 wherein the intracytoplasmic membrane is regulated by the same environmental stimuli which induce expression of the puc promoter of the Rhodobacter genus.

16. The method as recited in claim 11 wherein the protein is a multi-subunit membrane-associated protein complex.

17. The method as recited in claim 12, wherein the promoter is activated by lowering ambient oxigen tension.

18. The method as recited in claim 14 wherein the environmental stimuli are stimuli selected from the group consisting of oxygen tension and light.

19. A method for simultaneously producing and isolating a fusion protein, the method comprising:
   a) selecting a Rhodobacter species
   b) placing expression of the fusion protein under the control of an inducible promoter for synthesizing a Rhodobacter membrane compartment; and
   c) activating the promoter so as to synthesize a protein at the same time the membrane compartment is synthesized so that the protein is isolated by the membrane.

20. The method as recited in claim 19 wherein the promoter is the puf promoter from the Rhodobacter genus.

21. The method as recited in claim 19 the promoter is the puc promoter from the Rhodobacter genus.

22. The method as recited in claim 19 wherein the membrane compartment is a component of an inducible membrane system.

23. The method as recited in claim 19 wherein the promoter is activated by lowering ambient oxygen tension.

24. The method as recited in claim 19 wherein the promoter is activated by an environmental stimuli selected from the group consisting of oxygen tension and light.

25. A DNA sequence encoding a stable hairpin structure located between pufA and pufL genes in Rhodobacter comprising:
   a) an RNA stem-loop stabilizing region; and
   b) a transcript attached to said region that will result in the translation of a biologically active protein linked to an affinity peptide, and that will result in the simultaneous compartmentalization of the protein in its native state within Rhodobacter intracytoplasmic membrane.

26. The DNA sequence as recited in claim 25 wherein the protein comprises membrane-associated peptides.

27. The DNA sequence as recited in claim 25 wherein the protein forms a multi-subunit membrane associated protein complex.

* * * * *